United States Patent [19]

Garcin et al.

[11] Patent Number: 5,288,849
[45] Date of Patent: Feb. 22, 1994

[54] ALUMINA-BASED ADSORBENTS FOR THE PURIFICATION OF POLYOLEFINS

[75] Inventors: Eric Garcin, Montrouge; Claude-Bernard Cartier, Villeneuve-Saint-Georges; Eric Quemere, Cormeilles-En-Parisis, all of France

[73] Assignee: Rhone-Poulenc Chimie, Courbevoie, France

[21] Appl. No.: 631,476

[22] Filed: Dec. 21, 1990

Related U.S. Application Data

[62] Division of Ser. No. 466,917, Jan. 18, 1990, abandoned.

[30] Foreign Application Priority Data

Jan. 18, 1989 [FR] France ............... 89 00530

[51] Int. Cl.$^5$ .............................................. C08F 6/08
[52] U.S. Cl. .................... 528/482; 528/485; 528/488; 528/489
[58] Field of Search ............ 528/488, 482, 485, 489

[56] References Cited

U.S. PATENT DOCUMENTS

| | | | |
|---|---|---|---|
| 3,631,163 | 12/1971 | Witt | 528/482 |
| 3,962,199 | 6/1976 | Citron | 528/488 |
| 4,493,715 | 1/1985 | Hogan et al. | 502/415 |

FOREIGN PATENT DOCUMENTS 237175 9/1987 European Pat. Off.

Primary Examiner—Joseph L. Schofer
Assistant Examiner—Tom Weber
Attorney, Agent, or Firm—Burns, Doane, Swecker & Mathis

[57] ABSTRACT

Alumina-based adsorbents containing at least one compound of an alkali or alkaline earth metal, wherein the alkali or alkaline earth metal values are present in an amount ranging from 15 mmole to 100 mmole per 100 g of alumina, are useful for the adsorptive purification of polyolefins prepared by the polymerization of olefins in the presence of a metallic coordination catalyst, to remove contaminating catalyst metal values therefrom with but negligible monomer/solvent isomerization.

9 Claims, No Drawings

ALUMINA-BASED ADSORBENTS FOR THE PURIFICATION OF POLYOLEFINS

This application is a divisional of application Ser. No. 07/466,917, filed Jan. 18, 1990 now abandoned.

BACKGROUND OF THE INVENTION

1. Field of the Invention

The present invention relates to novel adsorbents for the purification of polyolefins and, more especially, to novel alumina-based adsorbents for the purification of polyolefins prepared by the polymerization of olefins in the presence of a system of coordination catalysts. This invention particularly relates to the purification of the reaction medium provided by the aforesaid polymerization process.

2. Description of the Prior Art

The polymerization of olefins is typically carried out in the presence of polymerization catalysts containing elements of Groups IVB, VB and VIB of the Periodic Table and, more particularly, containing vanadium, titanium and zirconium values. These catalysts also contain, as reducing agents, organometallic compounds (alkyl metallics), metallic hydrides or metal hydroxides. These catalysts are generally designated transition catalysts and have a high catalytic activity for the polymerization of olefins.

However, the polyolefins obtained are contaminated by metallic residues originating in the catalysts. It is thus strictly necessary to purify them prior to use, in order to prevent any coloration or degradation and to reduce their toxicity.

The processes for the polymerization of olefins generally entail apparatus for the recovery of the solvents and monomers contained in the polyolefins, such solvents and monomers being recycled back into the polymerization vessels. The presence of metals in these compounds promotes corrosion problems in the apparatus employed.

To purify the product polyolefin, it is known to this art to use different adsorbents, in particular the aluminas, for example.

Among the adsorbents used for such purpose, it is advantageous to utilize adsorbents in the form of pellets, which are handled more easily than powder or block articles of different shapes. In effect, a product in the form of pellets may be easily transported both for charging and discharging the purification columns, for example by use of various pneumatic systems.

From among such adsorbents, alumina is converted most readily into pellets. However, alumina, which is advantageous in view of its ease of handling and its good metal adsorption properties, presents a major disadvantage, i.e., it favors the isomerization of the solvents contained in the polyolefins, such as, for example, 1-butene.

Consequently, the solvents recovered cannot be completely recycled and most often they must be subjected to an additional purification to eliminate the isomerized products.

SUMMARY OF THE INVENTION

Accordingly, a major object of the present invention is the provision of improved alumina-based adsorbents for the purification of polyolefins, which improved adsorbents have but slight capacity for isomerizing olefin solvents/monomers and which are readily shaped into pellets, in particular, and, more generally, into any form permitting easy handling.

Briefly, the present invention features novel alumina-based adsorbent for the purification of polyolefins, said novel alumina-based adsorbents comprising at least one compound of an element selected from among the alkali or alkaline earth metals, in a proportion ranging from 15 mmole to 100 mmole of such alkali or alkaline earth metal per 100 g of alumina.

DETAILED DESCRIPTION OF THE PREFERRED EMBODIMENTS OF THE INVENTION

More particularly according to the present invention, except where otherwise indicated, all concentrations are expressed in millimoles of the element per 100 g of alumina calcined at 300° C. for 3 hours.

The adsorbents according to this invention have but a weak olefin isomerizing capability (power).

The isomerizing power of an adsorbent is determined by the following test:

The isomerizing power of the subject adsorbents is determined by carrying out an isomerizing test of 1-butene to cis- and trans-2-butene.

For this purpose, 500 mg of the ground adsorbent (particle sizes ranging from about 400 to 500 μm) are introduced into a reactor. The product is conditioned for 2 hours at 250° C. under a flowstream of helium, at a flow rate of 2.5 l/h.

The product is then heated to 400° C. and 1 ml butene is injected into the flowstream of helium.

Analysis of the outlet gases by chromatography makes it possible to measure the amount of 1-butene and cis-and trans-2-butene recovered.

By calculation, the theoretical thermodynamic equilibrium constant $K_{th}(T)$ and, from the result of the measurements, the actual equilibrium constant $K(T)$ are determined.

$$K_{th}(T) = \frac{[\text{cis-2-butene}]_e + [\text{trans-2-butene}]_e}{[\text{1-butene}]_e + [\text{cis-2-butene}]_e + [\text{trans-2-butene}]_e}$$

$$K(T) = \frac{[\text{cis-2-butene}] + [\text{trans-2-butene}]}{[\text{1-butene}] + [\text{cis-2-butene}] + [\text{trans-2-butene}]}$$

T is the temperature of the butene at the outlet of the reactor with the other values representing the concentrations upon exiting the reactor or at equilibrium $[]_e$ at the temperature T.

The isomerizing power or degree of isomerization $A(T)$ is given by the following formula:

$$A(T) = \frac{K(T)}{K_{th}(T)} \times 100$$

In one embodiment of the invention, the compound of the alkali or alkaline earth element is an oxide, hydroxide or salt thereof. Of course, mixtures of such compounds may be used according to the present invention.

Exemplary of such compounds, in addition to the oxides and hydroxides, are the sulfates, nitrates, halides, acetates, formates, carbonates and, more generally, salts of carboxylic acids.

The preferred compounds of the invention are the hydroxides and chlorides. These latter impart an important economic advantage by providing an adsorbent that effects a remarkably weak proportion of isomerization.

It is also possible to use a mixture of such alkali or alkaline earth elements. However, the total amount thereof preferably ranges from 15 mmole to 100 mmole per 100 g of the alumina.

Among such alkali and alkaline earth elements, sodium, potassium and calcium are the preferred.

However, if potassium is selected, the amount thereof preferably ranges from 15 mmole to 80 mmole.

Suitable aluminas according to the invention include those having a specific surface sufficient to provide an acceptable degree of adsorption of the alkali and alkaline earth metal values. Typically, the preferred aluminas have a specific surface area higher than 50 m$^2$/g.

The aluminas are produced by conventional methods, such as, for example, by precipitation or gel process, and the process of rapid dehydration of an alumina hydroxide.

The latter aluminas are the most preferred according to this invention.

The alkali or alkaline earth element or elements may be incorporated into the alumina by any technique, such as the coprecipitation of such element with the alumina, or impregnation of the alumina, prior to the shaping thereof, by a solution of the alkali or alkaline earth metal compound or compounds.

In a preferred embodiment of the invention, the process for the preparation of the subject adsorbents comprises impregnating the alumina, preferably in the form of pellets, with an aqueous solution of a salt or a hydroxide of the element to be incorporated, then drying the alumina and, optionally, subjecting it to a heat treatment to stabilize the specific surface area of the alumina.

The heat treatment is carried out at a temperature determined either as a function of the temperature at which the adsorbent is to be used, or the desired specific surface area. It may also be possible to carry out a heat treatment at a higher temperature, in order to effect an at least partial thermal degradation of the compound, for example into the oxide form. However, this degradation is not obligatory and, for example, is not necessary if compounds such as the chlorides, nitrates or hydroxides, are employed.

The adsorbents of the invention are particularly useful for the purification of polyolefins prepared by the polymerization of olefins in the presence of coordination catalysts by the adsorption of the contaminating metals introduced by said catalysts. In this manner, the olefins still present in the reaction mixture are purified without isomerization and may thus be recycled completely.

The process also makes it possible to purify the polyolefins themselves.

In order to further illustrate the present invention and the advantages thereof, the following specific examples are given, it being understood that same are intended only as illustrative and in nowise limitative.

In said examples to follow, the adsorbents indicated were prepared by treating an alumina agglomerated into pellets having a diameter of 1.5 mm–2.5 mm, a specific surface of 295 m$^2$/g measured by the BET method, a total pore volume of 0.5 cm$^3$/g and a residual sodium content ranging from 0.2 to 0.4% (by weight).

These alumina pellets are marketed by Rhone-Poulenc under the trademarks "A 1.5–2.5".

EXAMPLES 1 TO 18

The above alumina pellets were reactivated for 3 hours at 300° C. in air, then impregnated with a solution of a salt of the alkali or alkaline earth element or elements, or a compound thereof, such as a hydroxide of said element(s). The volume and the concentration of the solution were determined such as to provide the desired concentration of the element in the alumina.

The impregnated materials were then dried for 12 hours at 110° C., in air.

The isomerization powers of these dried materials were determined by the test described above.

The different results and characteristics of the adsorbents are reported in the Table which follows.

The results clearly show that an alumina containing an element such as sodium, potassium or calcium, has an isomerizing power markedly lower than that of an untreated alumina (Example 1). The examples further show that the reduction of the isomerizing power of the alumina was effected over a definite range of concentrations.

Therefore, untreated aluminas which contain sodium as an impurity were not suitable, as the sodium concentration was too low.

The same was also true for alumina containing a high percentage of sodium (5% and more) used in particular for the adsorption of acid impurities.

Aluminas containing an element such as lithium, strontium and magnesium also display an isomerizing power that is clearly lower than that of an untreated alumina (Example 1).

TABLE

| Example | Element X | Impregnating solution | Concentration of X in adsorbent (mmole/100 g Al$_2$O$_3$) | Isomerizing power A% |
|---|---|---|---|---|
| 1(1) | — | — | 0 | 63% |
| 2 | Na | NaOH | 25 | 14% |
| 3 | Na | NaOH | 62 | 5% |
| 4(1) | Na | NaOH | 250 | 54% |
| 5 | K | KOH | 26 | 8% |
| 6 | K | KOH | 68 | 14% |
| 7 | K | KOH | 15 | 16% |
| 8(2) | Ca | Ca(COOCH$_3$)$_2$ | 44 | 13% |
| 9(2) | Ca | Ca(OOCCH$_3$)$_2$ | 18 | 21% |
| 10(2) | Na | NaOOCCH$_3$ | 36 | 9% |
| 11(2) | Na | CH$_3$COONa | 90 | 9% |
| 12 | Na | NaCl | 65 | 1% |
| 13(1) | Na | NaOH | 12 | 42% |
| 14(1) | K | KOH | 130 | 77% |
| 15(2) | Li | CH$_3$COOLi | 45 | 14% |
| 16(2) | Sr | Sr(OOCCH$_3$)$_2$ | 65 | 36% |
| 17(2) | Mg | Mg(OOCH$_3$)$_2$ | 65 | 36% |

TABLE-continued

| Example | Element X | Impregnating solution | Concentration of X in adsorbent (mmole/100 g Al$_2$O$_3$) | Isomerizing power A% |
|---|---|---|---|---|
| 18 | Ca | CaCl$_2$ | 45 | 11% |

(1)Comparative experiments.
(2)Calcined at 600° C. for three hours after impregnation.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. In a process for the adsorptive purification of a polyolefin prepared by the polymerization of an olefin in the presence of a metallic coordination catalyst, to remove contaminating catalyst metal values therefrom, which comprises utilizing as the adsorbent therefore, an alumina substrate having incorporated therein at least one compound of an alkali or alkaline earth metal, said alkali or alkaline earth metal values being present therein in an amount ranging from 15 mmole to 100 mmole per 100 g of alumina substrate.

2. The process as defined by claim 1, wherein said at least one compound of an alkali or alkaline earth metal comprises an oxide, hydroxide or salt thereof.

3. The process as defined by claim 1, wherein said at least one compound of an alkali or alkaline earth metal comprises a sulfate, nitrate, halide, acetate, formate, carbonate, or carboxylic acid salt thereof.

4. The process as defined by claim 1, wherein said at least one compound of an alkali or alkaline earth metal comprises a chloride or hydroxide thereof.

5. The process as defined by claim 1, wherein said alkali or alkaline earth metal comprises sodium, potassium or calcium.

6. The process as defined by claim 5, wherein said alkali or alkaline earth metal comprises potassium, said potassium values being present in an amount ranging from 15 mmole to 80 mmole per 100 g of alumina substrate.

7. The process as defined by claim 1, wherein said alumina substrate has a specific surface area of greater than 50 m$^2$/g.

8. The process as defined by claim 1, wherein said alumina substrate comprises pelletized alumina particulates.

9. The process as defined by claim 1, wherein said substrate has been prepared by rapid dehydration of an alumina hydroxide.

* * * * *